(12) United States Patent
Berger et al.

(10) Patent No.: US 8,414,594 B2
(45) Date of Patent: Apr. 9, 2013

(54) MAGAZINE FOR RECEIVING AT LEAST ONE BONE SCREW AND BONE PLATE HAVING SUCH A MAGAZINE

(75) Inventors: Jens Berger, Tuttlingen (DE); Joerg Schumacher, Teltow (DE); Ralph Linke, Steisslingen (DE)

(73) Assignee: Aesculap AG, Tuttlingen (DE)

( * ) Notice: Subject to any disclaimer, the term of this patent is extended or adjusted under 35 U.S.C. 154(b) by 199 days.

(21) Appl. No.: 12/804,273

(22) Filed: Jul. 16, 2010

(65) Prior Publication Data

US 2011/0004254 A1  Jan. 6, 2011

Related U.S. Application Data

(63) Continuation of application No. PCT/EP2008/010011, filed on Nov. 26, 2008.

(30) Foreign Application Priority Data

Feb. 21, 2008 (DE) .......................... 10 2008 010 333

(51) Int. Cl.
*A61B 17/58* (2006.01)
*A61B 17/80* (2006.01)

(52) U.S. Cl.
USPC ............................................. 606/104; 606/96

(58) Field of Classification Search ................ 606/86 R, 606/96, 99, 104, 289; 206/338, 339, 345, 206/347, 437, 438
See application file for complete search history.

(56) References Cited

U.S. PATENT DOCUMENTS

| | | | | | |
|---|---|---|---|---|---|
| 3,812,961 | A | * | 5/1974 | Merrick et al. | ................ 206/338 |
| 4,299,221 | A | * | 11/1981 | Phillips et al. | .................. 604/30 |
| 5,129,292 | A | * | 7/1992 | Albert | .............................. 81/452 |
| 6,128,982 | A | * | 10/2000 | Gwin, Sr. | ......................... 81/452 |
| 6,328,746 | B1 | | 12/2001 | Gambale | |
| 2004/0204717 | A1 | * | 10/2004 | Fanger et al. | .................... 606/96 |
| 2005/0177163 | A1 | | 8/2005 | Abdou | |
| 2005/0283155 | A1 | | 12/2005 | Jacene et al. | |
| 2006/0149250 | A1 | | 7/2006 | Castaneda et al. | |
| 2006/0229618 | A1 | | 10/2006 | Dube | |

FOREIGN PATENT DOCUMENTS

WO  2007/070196  6/2007

* cited by examiner

*Primary Examiner* — Kevin T Truong
*Assistant Examiner* — Christian Sevilla
(74) *Attorney, Agent, or Firm* — Lipsitz & McAllister, LLC

(57) ABSTRACT

To facilitate the insertion of bone screws into a bone plate, a magazine for receiving at least one bone screw is proposed, which comprises a device for releasably securing the magazine to a bone plate, a receiving chamber extending continuously from the upper side to the underside of the magazine, a bone screw being arranged in the receiving chamber in such a way that when the magazine is secured to the bone plate, the distal tip of the bone screw is directed at a screw-in opening in the bone plate, and the proximal end of the bone screw is accessible to a screwing-in tool from the upper side of the magazine, and a fixing device for releasably fixing the bone screw in the receiving chamber. The invention also relates to a bone plate having at least one such magazine releasably secured thereto.

20 Claims, 12 Drawing Sheets

MAGAZINE FOR RECEIVING AT LEAST ONE BONE SCREW AND BONE PLATE HAVING SUCH A MAGAZINE

This application is a continuation of international application number PCT/EP2008/010011 filed on Nov. 26, 2008 and claims the benefit of German Patent Application No. 10 2008 010 333.0 filed on Feb. 21, 2008.

The present disclosure relates to the subject matter disclosed in international application number PCT/EP2008/010011 of Nov. 26, 2008 and German application number 10 2008 010 333.0 of Feb. 21, 2008, which are incorporated herein by reference in their entirety and for all purposes.

BACKGROUND OF THE INVENTION

The invention relates to a magazine for receiving at least one bone screw.

The invention also relates to a bone plate having such a magazine mounted thereon.

Bone plates normally have several screw-in openings through which bone screws are screwed in order to fix the bone plates to bone parts. Screwing-in these bone screws may prove difficult because the surgical sites are often not easy to access and, in the majority of cases, the bone screws are relatively short. There is therefore a risk of the bone screws being misaligned. There is also a risk of dropping a bone screw within the surgical site and of then having to search for it laboriously.

It is known to place guide sleeves on bone plates in order to impart guidance to the bone screws while these are being screwed in. For example, a bone plate is described in US 2006/0149250 A1, wherein sleeve-shaped guides can be screwed into the screw-in openings and then have to be individually removed from the screw-in openings again after the bone screws have been screwed in. A precondition of this construction is that the screw-in openings have a screw-in thread for the guide sleeves. This therefore involves relatively high constructional expenditure. Also, the removal of the guide sleeves is laborious as a corresponding guide sleeve has to be screwed out of each screw-in opening.

A template is described in US 2005/0177163 A1, which can be placed on a bone plate using a handle. This template has guide openings for bone screws. After the bone screws have been screwed in, the template can be removed again in its entirety from the bone plate using a handle. Difficulties are also encountered with use of this known construction as the bone screws have to be inserted into the guide openings of the template. This may also be problematic at surgical sites that are difficult to access.

The object of the invention is to provide a magazine for receiving at least one bone screw, with which the screwing of a bone screw into a bone plate is facilitated.

SUMMARY OF THE INVENTION

This object is accomplished, in accordance with the invention, by a magazine for receiving at least one bone screw, comprising a device for releasably securing the magazine to a bone plate, further comprising a receiving chamber extending continuously from the upper side to the underside of the magazine, a bone screw being arranged in the receiving chamber in such a way that when the magazine is secured to the bone plate, the distal tip of the bone screw is directed at a screw-in opening in the bone plate, and the proximal end of the bone screw is accessible to a screwing-in tool from the upper side of the magazine, and also comprising a fixing device for releasably fixing the bone screw in the receiving chamber.

Owing to the releasable mounting of a magazine on the bone plate, the bone screw arranged in the receiving chamber of the magazine is placed in a screw-in position in which it is directed at the respective screw-in opening and is therefore already positioned on the bone plate. When inserting the bone plate, it is inserted together with the magazine, so that there is no longer any necessity for a complicated insertion procedure for a bone screw. Once the bone plate is positioned in the desired manner at the surgical site, it is easily possible, with a screwing-in tool, to advance the bone screw held in screw-in position in the magazine in the distal direction, i.e., in the direction towards the screw-in opening and the bone located under the screw-in opening and to then screw it in through the screw-in opening into the bone. When the bone screw has been screwed in this manner into the bone plate, the magazine, which is releasably secured to the bone plate, may be removed.

The laborious insertion procedure for the bone screw is dispensed with by using a magazine in which the bone screw is already held. Also, the surgeon finds the bone screw already in the desired screw-in position and screw-in direction relative to the bone plate, so that there is no longer any necessity for any adjusting procedures.

In particular, the receiving chamber may be in the form of a channel.

It is particularly advantageous for the receiving chamber to form a longitudinal guide for the bone screw, along which the bone screw is advanceable, while being screwed-in, in the distal direction through the screw-in opening. Therefore, during the screwing-in, the surgeon need no longer pay any attention to the screwing-in direction, this being specified and maintained by the guidance in the longitudinal guide of the magazine.

In a first preferred embodiment, it is provided that the bone screw abuts with a frictional fit on the inside wall of the receiving chamber and is thereby releasably held in the receiving chamber. The frictional fit can be overcome during the screwing-in, but the frictional fit is adequate to hold the bone screw, during insertion of the bone plate into the surgical site, in the prepared screw-in position.

In another preferred embodiment, it is provided that the fixing device comprises at least one elastic latching projection and at least one latching recess cooperating with the latching projection. An elastic latching connection is thereby established between bone screw and magazine, which can be overcome by the surgeon during the screwing-in.

For example, at least one elastic latching projection on the magazine extends into the receiving chamber and enters a recess on the bone screw.

Such a latching projection may be arranged directly on the magazine itself or else on a retaining element inserted into the receiving chamber. A sleeve, for example, can be inserted into the receiving chamber. The sleeve is secured in the receiving chamber and, in turn, carries an elastic latching projection for the bone screw. This retaining element may be adapted to different dimensions of the bone screw, so that a magazine may be used for bone screws of different dimensions.

The latching projection on the magazine may, for example, enter a latching recess in the form of a circumferential groove provided on the bone screw.

In a further preferred embodiment it is provided that the fixing device comprises a projection on the bone screw or the receiving chamber, and a recess on the receiving chamber or the bone screw for engagement of the projection in the recess, and that the projection and/or the recess are helically constructed in the manner of a thread. Fixation is, therefore, effected by screwing-in, and, accordingly, release is effected by rotational movement of the bone screw relative to the receiving chamber and, consequently, screwing of the bone screw out of the receiving chamber.

In particular, the pitch of the helical projection and/or recess may correspond to the pitch of the thread of the bone screw, so that the screwing of the bone screw out of the receiving chamber and, consequently, the release from the receiving chamber may take place simultaneously with the screwing of the bone screw into the bone.

In accordance with a preferred embodiment, the projection or recess on the bone screw is at least partially formed by the thread of the bone screw. In this case, it is expedient for the core diameter of the bone screw to increase in the upper part, so that an abutment on the bone plate is thereby enabled in this upper thread area, by means of which the bone screw then tensions the bone plate against the bone.

The device for the releasable securing of the magazine to the bone plate may, in accordance with a preferred embodiment, comprise elastic latching elements which hold the magazine by means of a snap-in connection on the bone plate. It is then possible to snap the magazine onto a bone plate and to also release it again in a corresponding manner without the necessity for additional tools or attachment elements.

Accordingly, the magazine may carry on its underside latching elements which, when the magazine is mounted on the bone plate, engage the bone plate around its outer side. This construction makes it possible to also secure magazines to bone plates that are not specially adapted to the geometry of the magazines. It suffices for the latching elements of the magazine to engage around the outer contour of the bone plate.

In particular, the magazine may have on its underside a receiving recess for receiving at least part of the bone plate, with the rim of the receiving recess, as elastic latching element, engaging around the outer side of the bone plate located in the receiving recess.

In order to achieve a secure positioning of the bone plate relative to the magazine, it is possible to arrange positioning projections and recesses on the magazine and on the bone plate, which engage with one another and thereby align the magazine relative to the bone plate.

For example, the magazine may carry on its underside a downwardly projecting positioning pin which enters a positioning opening on the bone plate when the magazine is mounted on the bone plate.

It is expedient for a handling grip to be secured to the magazine. This can then simultaneously serve for handling the entire constructional unit consisting of bone plate and magazine when the magazine is secured to the bone plate. In a preferred embodiment, it is provided that the magazine comprises several adjacent receiving chambers, in each of which a bone screw is arranged in such a way that when the magazine is mounted on the bone plate, the bone screw is directed at one of several screw-in openings in the bone plate. This also enables several bone screws to be simultaneously positioned relative to several screw-in openings in the bone plate, namely with a single magazine which is releasably secured to the bone plate.

In a particularly preferred embodiment, it may be provided that the magazine comprises a holder on which the device for releasable fixation to the bone plate is arranged, and a housing which is displaceably mounted on the holder and comprises the receiving chamber or optionally the several receiving chambers. In this case, the displacement may be a translation or rotation or also a superimposed movement including translation and rotation. Owing to the displaceability of the housing on the holder, it is possible to displace the receiving chamber or the receiving chambers into a position in which they are in alignment with a certain screw-in opening; in another position they are not. It is, for example, possible to keep bone screws of different sizes in different receiving chambers and by displacing the housing to select which of the bone screws is brought into alignment with a certain screw-in opening.

It is also possible for the housing to comprise in addition to the receiving chamber or the receiving chambers for bone screws at least one further through-opening which extends continuously from the upper side to the underside and, upon displacement of the housing, is alignable with one or more screw-in openings in the bone plate. Such a through-opening may, for example, be constructed as drill guide and allow the surgeon to drill a hole in the bone located under the bone plate, through a screw-in opening, namely in the direction of the through-opening. A marking operation could also be carried out through the though-opening, for example, using a punch, or the through-opening could accommodate a tool for cutting a thread in the bone.

In particular, it may be provided that the through-opening forms a receiving chamber for a spike-shaped pin which is mounted for longitudinal displacement in the receiving chamber. Such a spike-shaped pin can be used as punch when it is displaced in the distal direction towards the bone and then forms a depression in the bone with a tip.

It is expedient for the spike-shaped pin to be displaced by a spring into a proximal end position and to be displaceable in the distal direction against the action of this spring.

The housing can be mounted for longitudinal displacement on the holder. In a particularly preferred embodiment, it is provided that the housing is mounted for rotation on the holder in such a way that in different angular positions different receiving chambers and through-openings are alignable with the screw-in openings. The housing is thus mounted in the manner of a turret on the holder.

In this case, it is advantageous for a rotary handle to be arranged on the housing for rotating the housing relative to the holder.

The invention also relates to a bone plate with at least one magazine having the features discussed above releasably mounted thereon.

The following description of preferred embodiments of the invention serves in conjunction with the drawings for further explanation.

Figure 1:
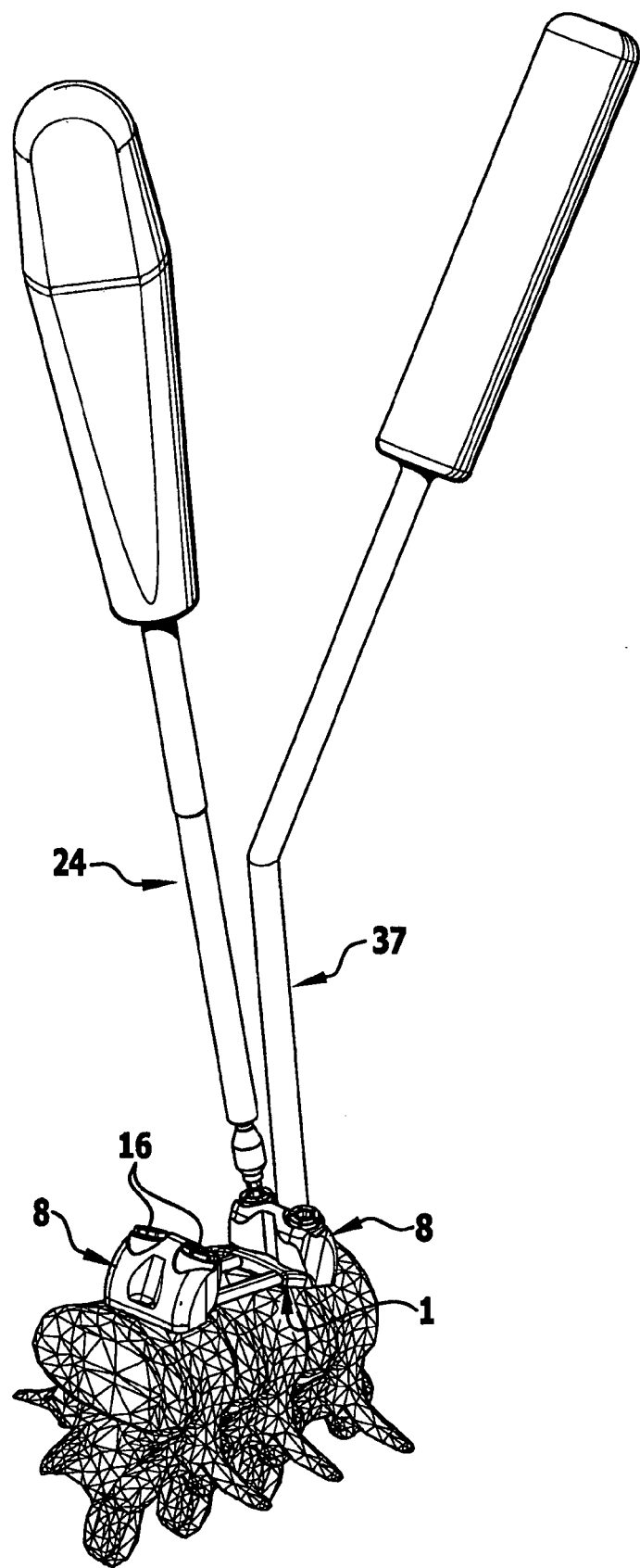
FIG. 1 shows a perspective view of a bone plate in abutment with vertebrae with two bone screw magazines mounted thereon and a screwing-in tool.
Figure 2:
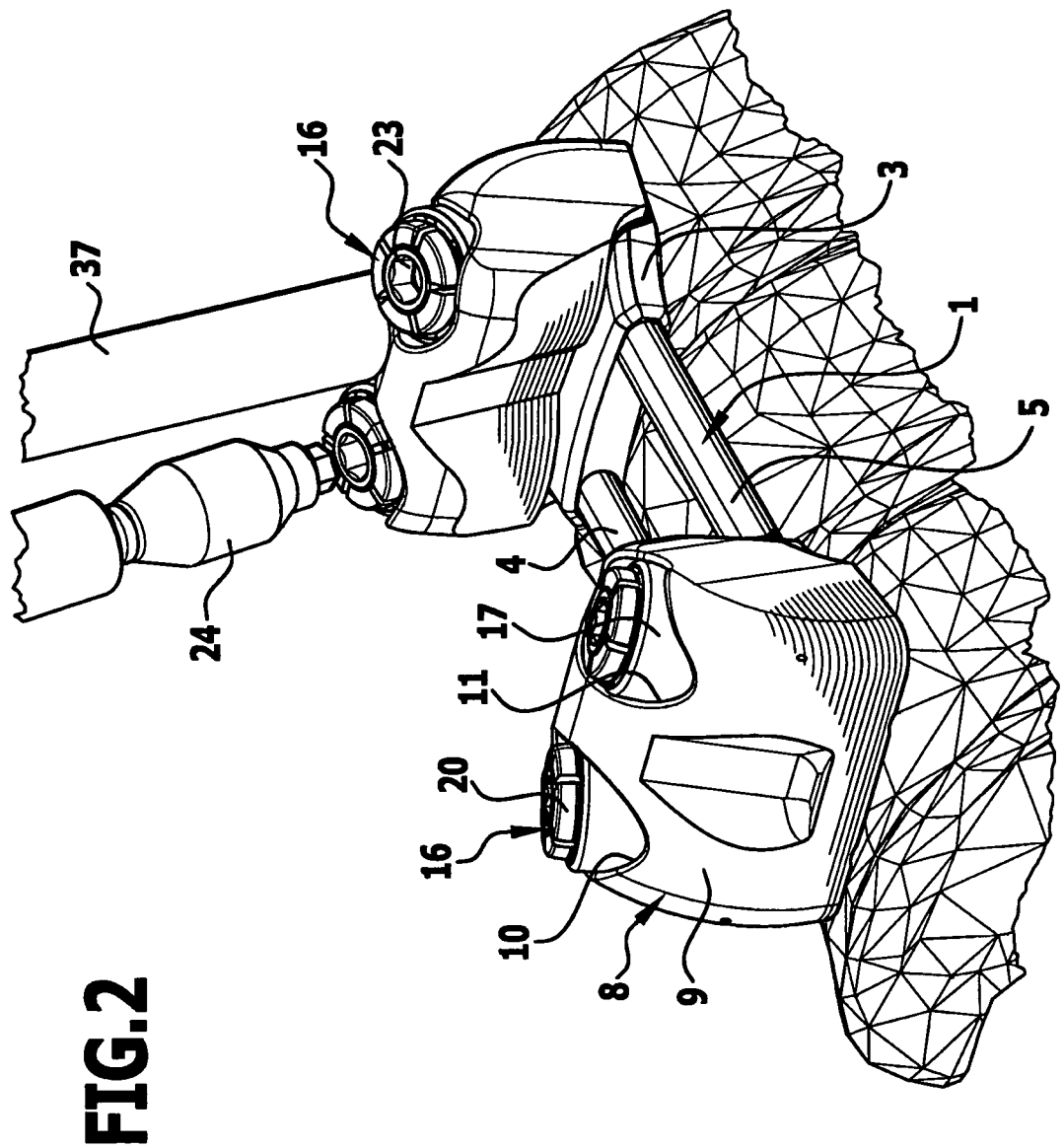
FIG. 2 shows an enlarged detailed view of the bone plate of FIG. 1.
Figure 3:
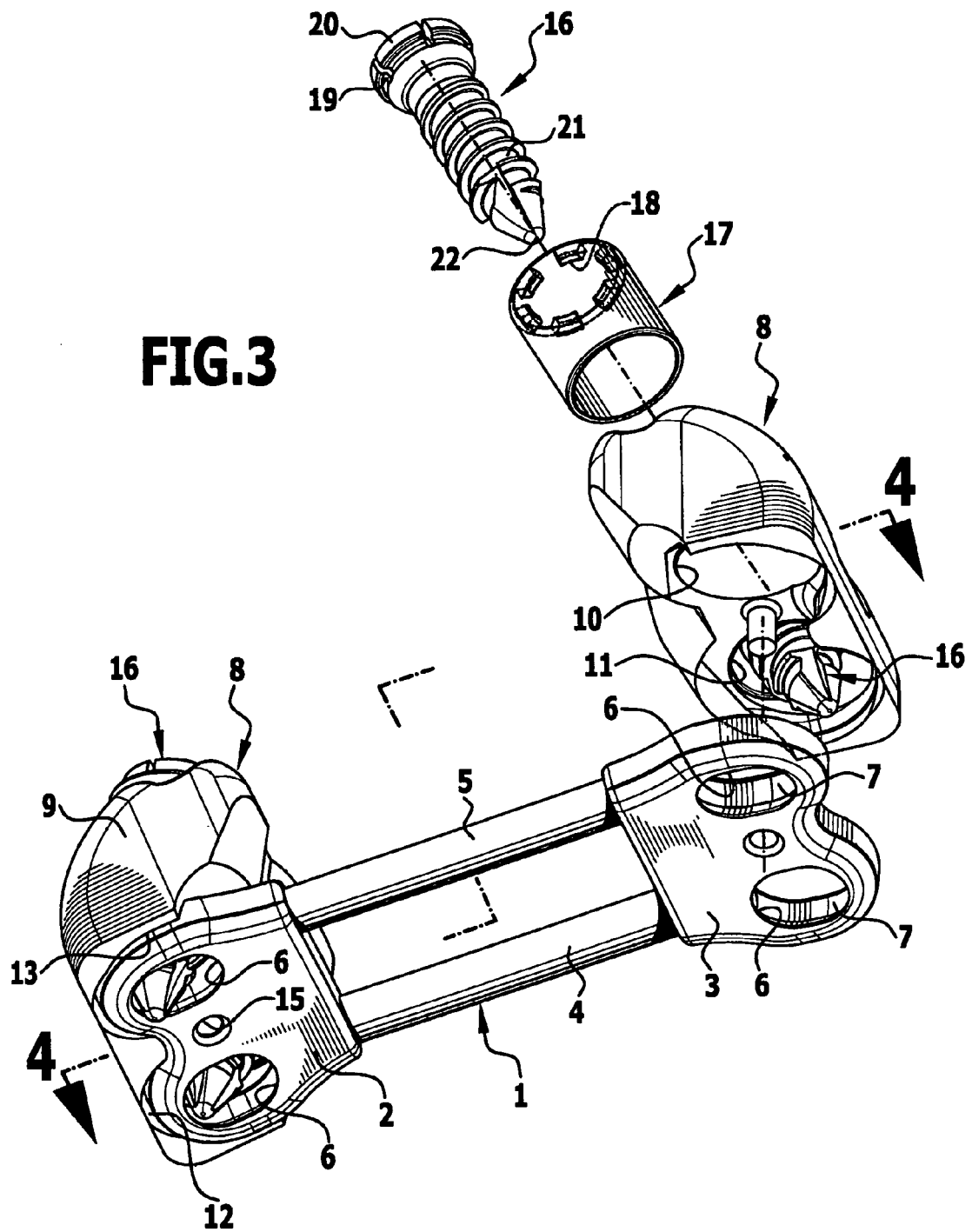
FIG. 3 shows a perspective exploded representation of the bone plate of FIG. 1, viewed from the underside of the bone plate.
Figure 4:
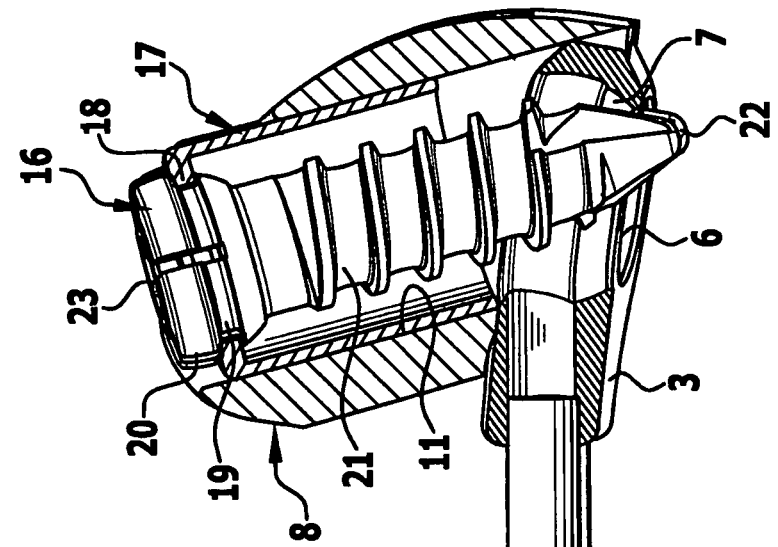
FIG. 4 shows a sectional view taken along line 4-4 in FIG. 3.

The drawings show, by way of example, a bone plate 1 which, in this case, comprises two end pieces 2, 3, which are connected to each other by two rod-shaped connecting elements 4, 5. The end pieces 2, 3 are of plate-shaped construction and each have two adjacent screw-in openings 6 which with rounded-off side walls 7 taper towards the underside. The connecting elements 4, 5 may consist of a physiologically compatible metal, for example, of titanium or of a titanium alloy, while the end pieces 2, 3 may consist of a physiologically compatible and biocompatible plastic material, for example, of polyetheretherketone (PEEK). The plastic material may be optionally reinforced by fibers, for example, by carbon fibers.

Onto this bone plate 1, magazines 8 can be mounted on each of the two end pieces 2, 3. The magazines are identical in construction. They can be selectively mounted on one end piece or the other end piece. Therefore, only one of the two magazines 8 will be explained in greater detail below.

The magazine 8 shown in FIGS. 1 to 6 comprises a one-part housing block 9 with two adjacent, channel-shaped receiving chambers 10, 11, which extend through the entire housing block 9 from the upper side to the underside.

The housing block 9 can be releasably mounted on a respective one of the two end pieces 2, 3. To secure the housing block 9 to the end piece 2 or 3, the housing block 9 has on its underside a recess 12, which is adapted to the outer contour of the end piece, and the side rim 13 of which projects inwards to a slight extent into the recess 12. The housing block 9 is made of a sterilizable plastic material, for example, of polyetheretherketone, acrylonitrile butadiene styrene, polypropylene, polyethylene, polysulfone, polyetherketone, polyoxymethylene or polystyrene. These materials are so elastic that the rim 13 is also elastically bendable outwards. As a result, the housing block 9 can be pressed onto an end piece 2 or 3, in the course of which the rim 13 of the recess 12 slides along the outer contour of the end piece 2 or 3 and then engages around the end piece 2, 3 once it enters the recess 12. An elastic latching connection or snap-in connection is thereby established, by means of which the housing block 9 is releasably secured to the end piece 2 or 3. To release it, the housing block 9 only has to be pulled off the end piece 2 or 3 with force, in the course of which the rim 13 is elastically bent outwards and releases the end piece 2 or 3.

For exact positioning of the housing block 9, it has on its underside a pin-shaped projection 14, which enters an opening 15 in the end piece 2 or 3. This opening 15 is arranged between the two screw-in openings 6 of the end piece 2, 3.

When the housing block 9 is mounted in this way on an end piece 2, the receiving chambers 10, 11 of the housing block 9 are in alignment with the two screw-in openings 6, so that these receiving chambers 10, 11 form a channel directed from the upper side of the housing block 9 onto the two screw-in openings 6.

In the embodiment of FIGS. 1 to 6, a bone screw 16 is received in each of these receiving chambers 10, 11. The bone screw 16 is first held in an initial position in the receiving chamber 10, 11. In order to secure the bone screw 16 in this initial position in the housing block 9, there is inserted, in the embodiment of FIGS. 1 to 3, in each receiving chamber 10, 11 a retaining sleeve 17, which may be secured in the receiving chamber 10 with a frictional fit or in some other way, for example, also by an adhesive connection or by a latching connection. This retaining sleeve 17 carries at its upper rim inwardly protruding latching projections 18 which enter a circumferential groove 19 in the bone screw 16. This circumferential groove 19 is arranged in the area of the head 20 of the bone screw 16. In the initial position of the bone screw 16, the head 20 is therefore arranged at the upper end of the retaining sleeve 17 and protrudes slightly upwards over this retaining sleeve 17. The threaded shaft 21 of the bone screw 16 adjoining the head 20 then extends over the length of the receiving chamber, with the tip 22 of the bone screw 16 entering the screw-in opening 6 to a slight extent, so that the tip 22 protrudes only very slightly downwards beyond the bone plate 1.

An internal polygonal socket 23 is arranged in the head 20 of the bone screw 16. This forms a receptacle for insertion therein of a screwing-in tool 24 with positive locking.

Figure 5:
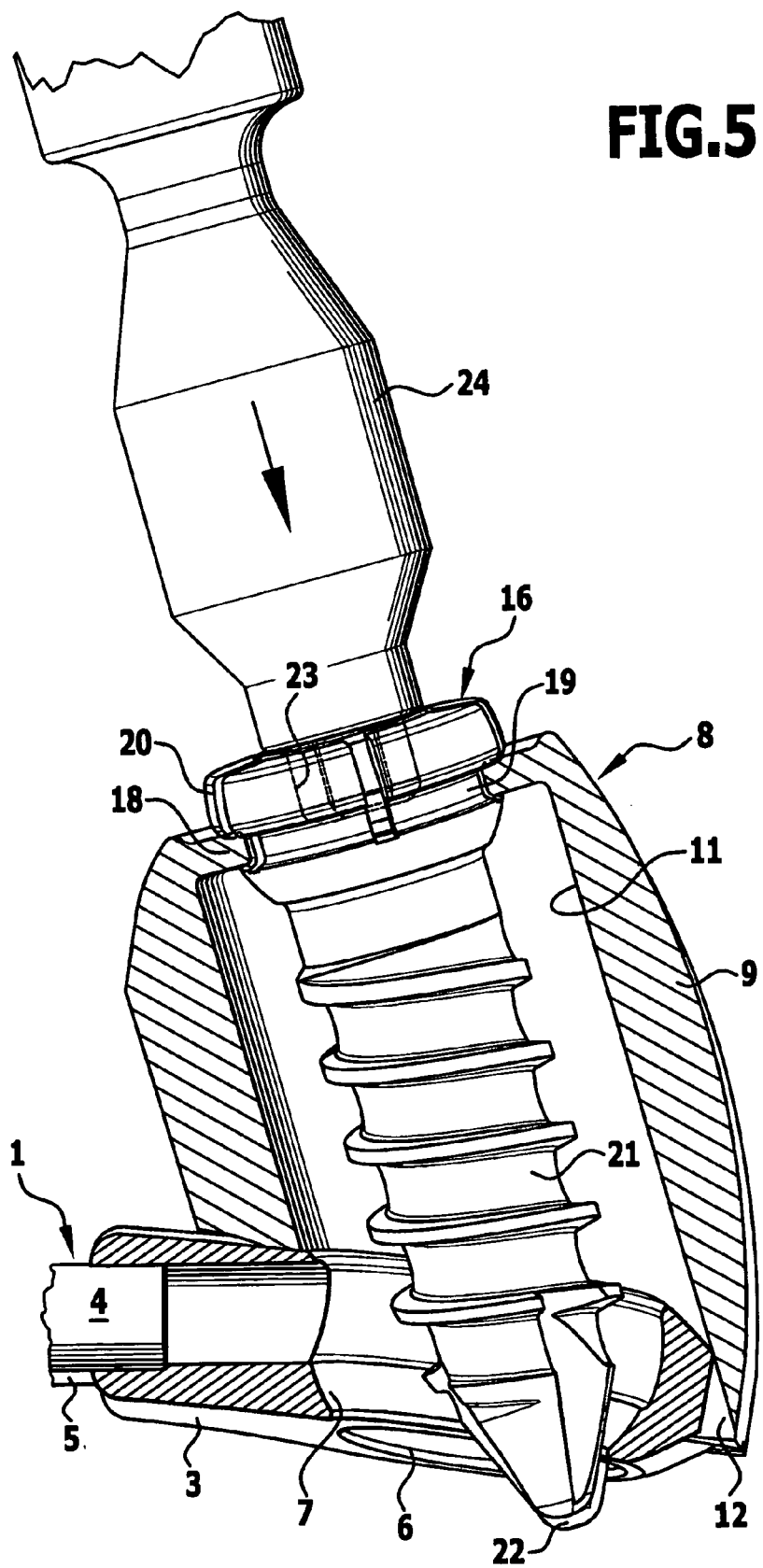
FIG. 5 shows a partial view of a modified embodiment of a magazine mounted on a bone plate with latching projections arranged directly on the magazine.
Figure 6:
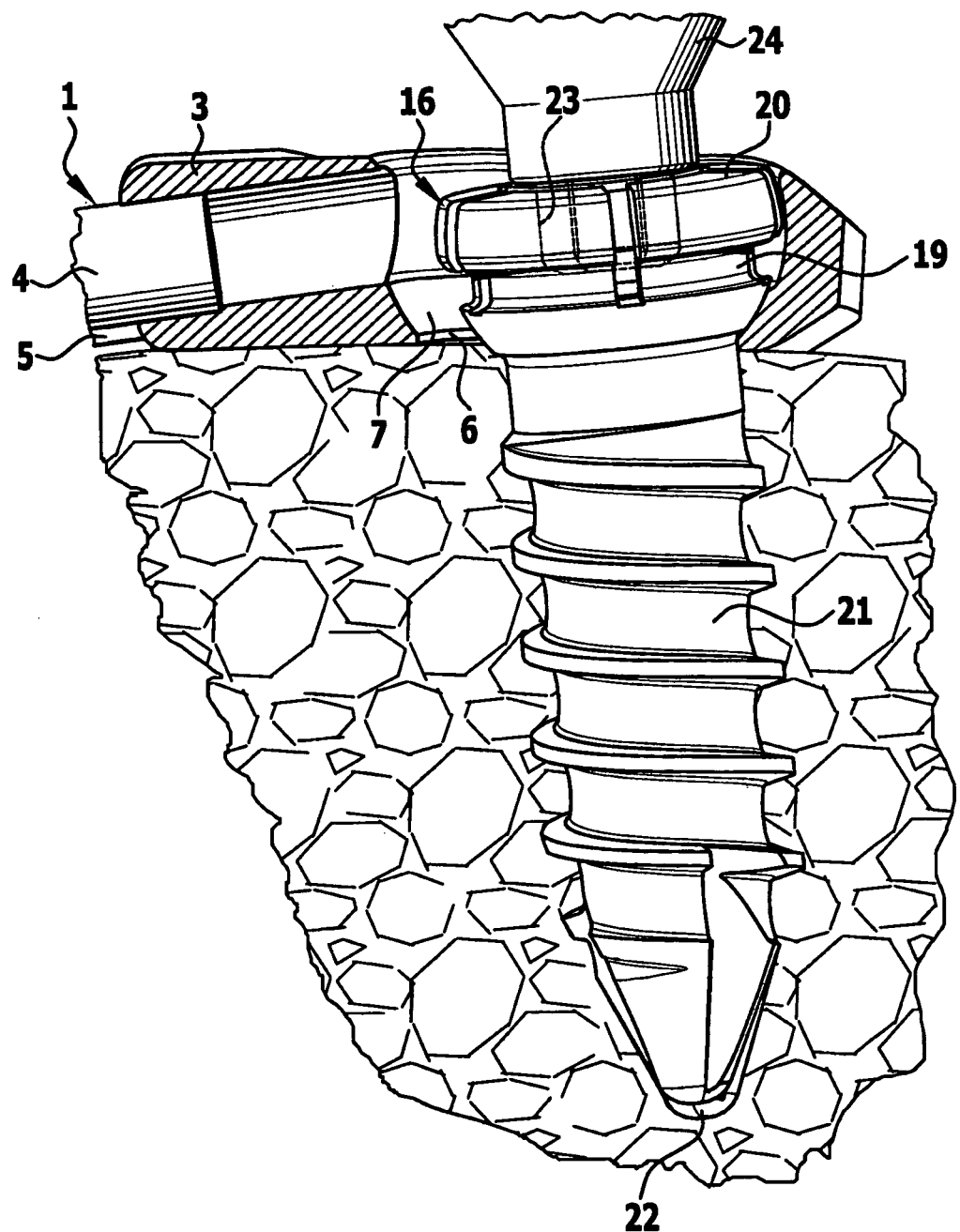
FIG. 6 shows a sectional view of part of the bone plate after the bone screw has been screwed in fully and after the magazine has been removed.
Figure 7:
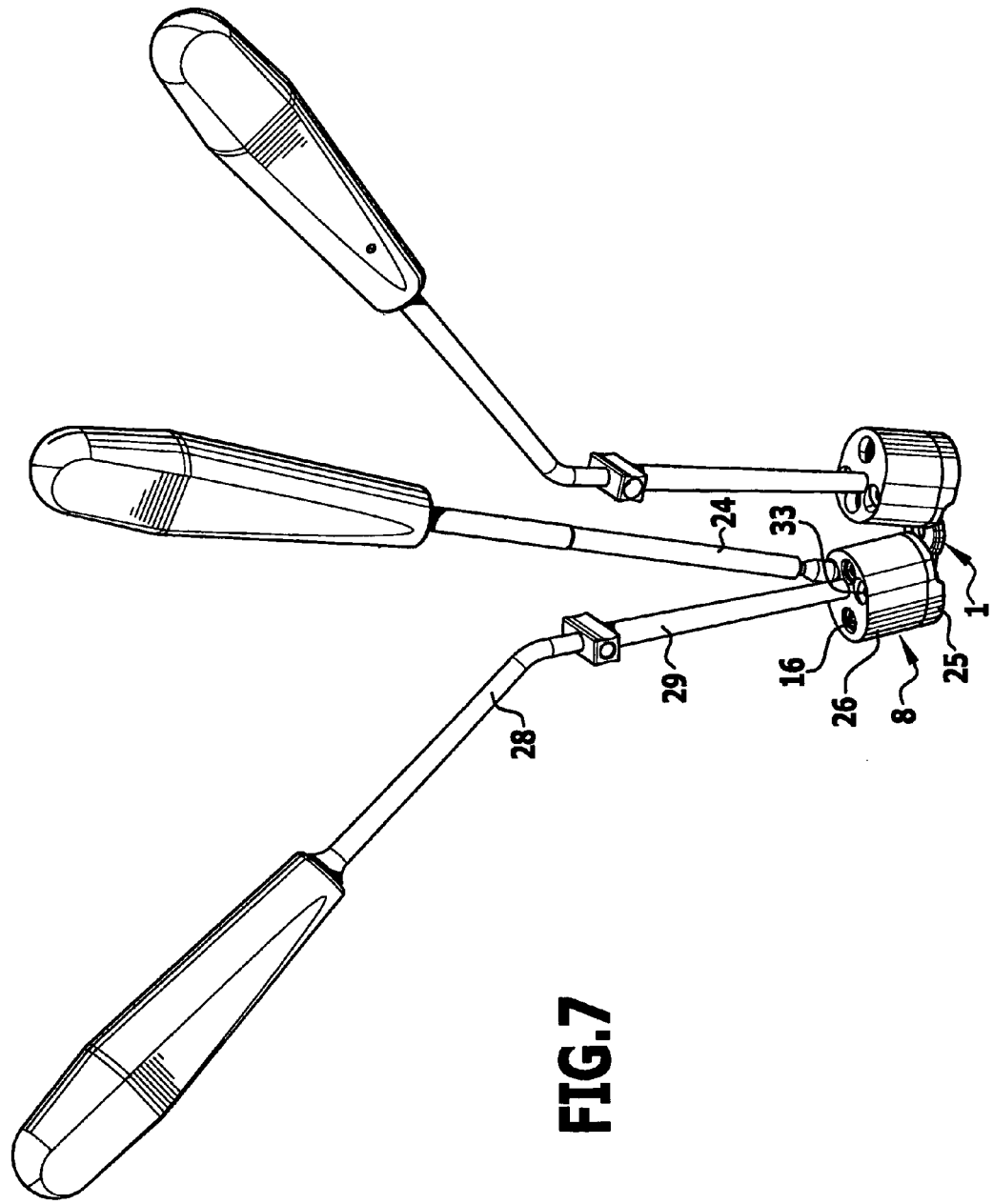
FIG. 7 shows a perspective view of a bone plate with two magazines having a rotatable housing.
Figure 8:
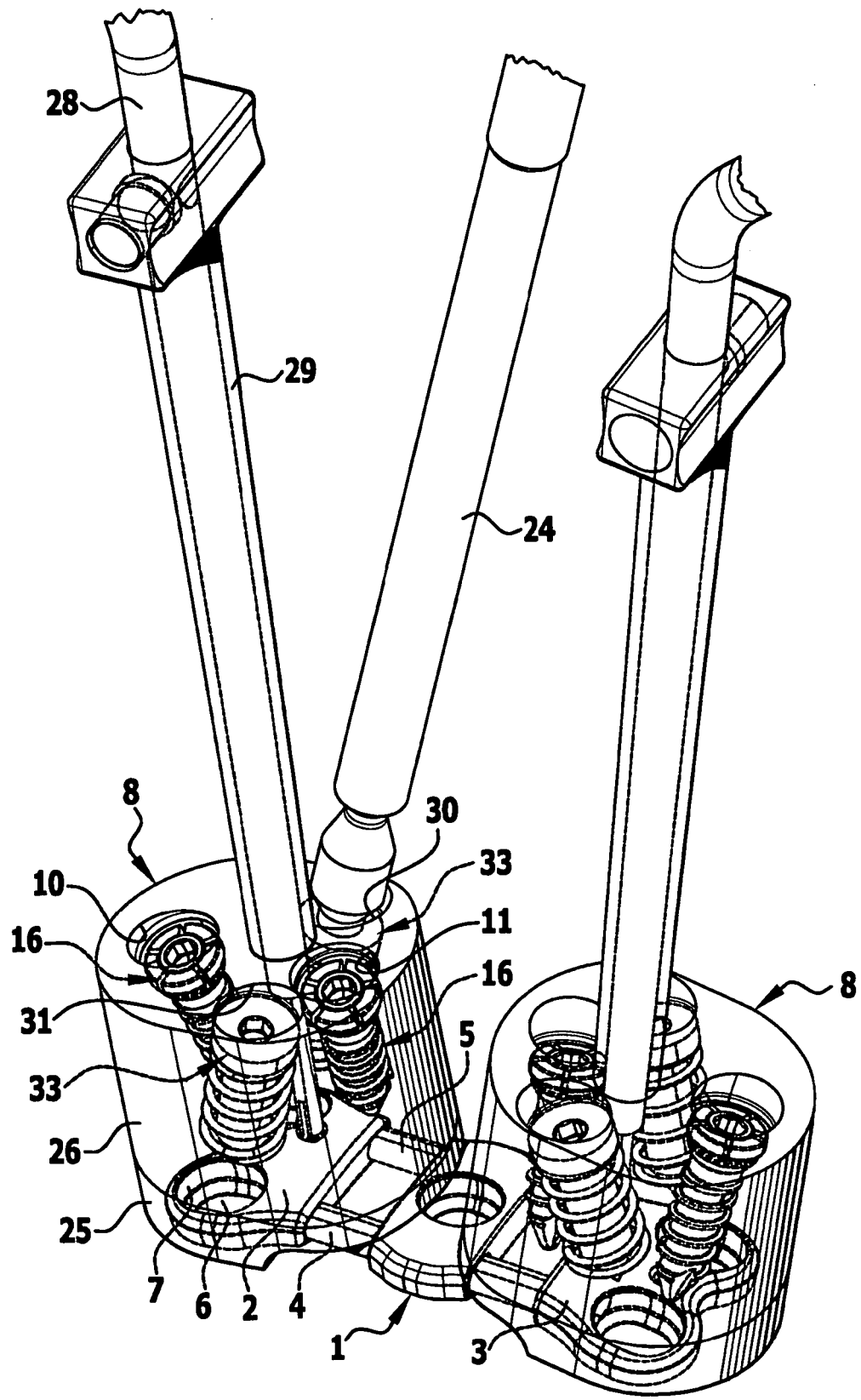
FIG. 8 shows an enlarged view of the bone plate of FIG. 7 with magazines for receiving bone screws and displaceable spike-shaped pins.

A similar configuration is shown in the embodiment of FIG. 5. Like parts are therefore given like reference numerals. Unlike the embodiment of FIGS. 1 to 4, there is no retaining sleeve 17 in this embodiment. In this embodiment, the latching projections 18 are arranged directly on the housing block 9.

Figure 9:
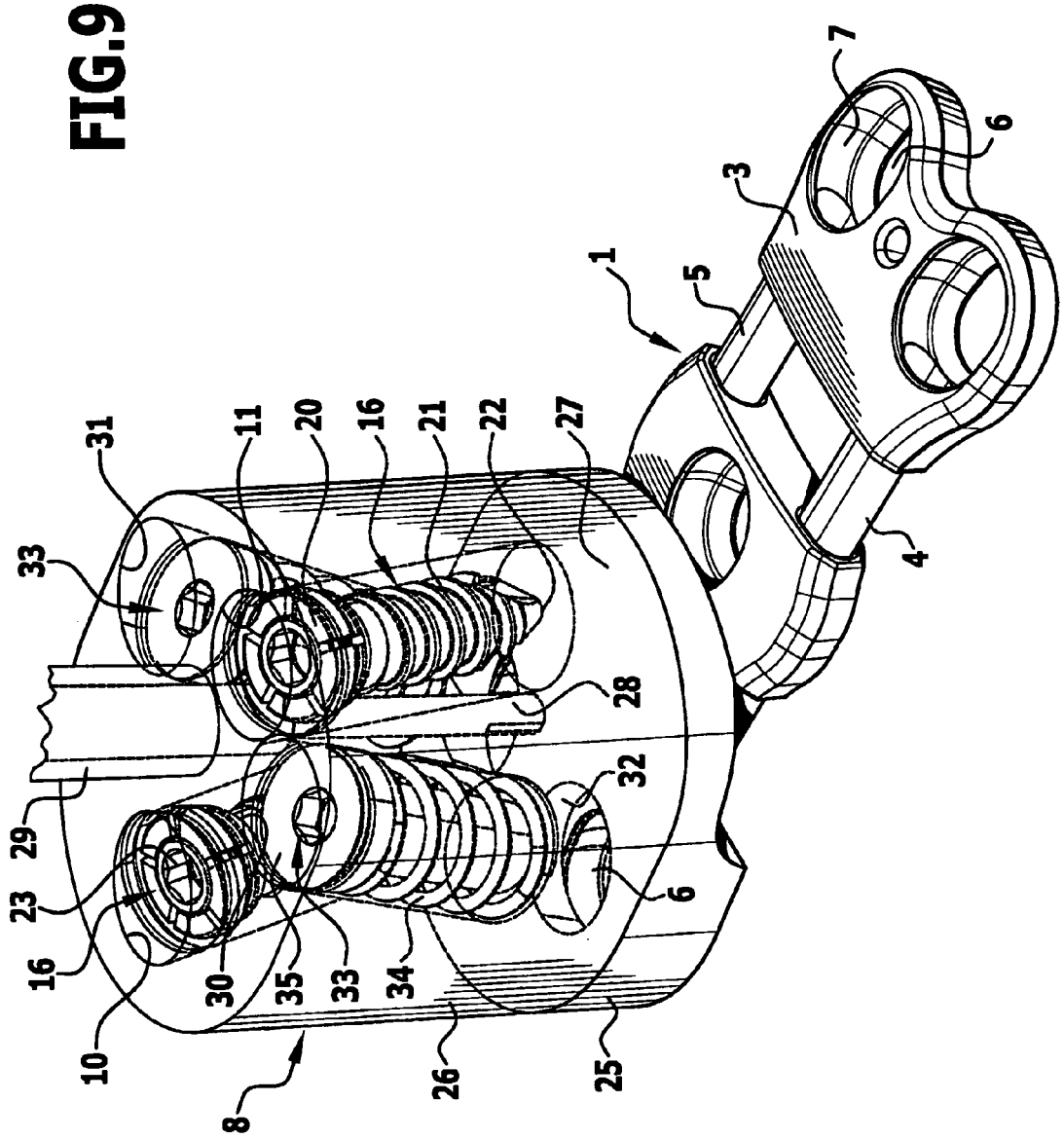
FIG. 9 shows a perspective view of a bone plate having mounted thereon a magazine with a rotatable housing, with the screw-in openings in alignment with displaceable spike-shaped pins.
Figure 10:
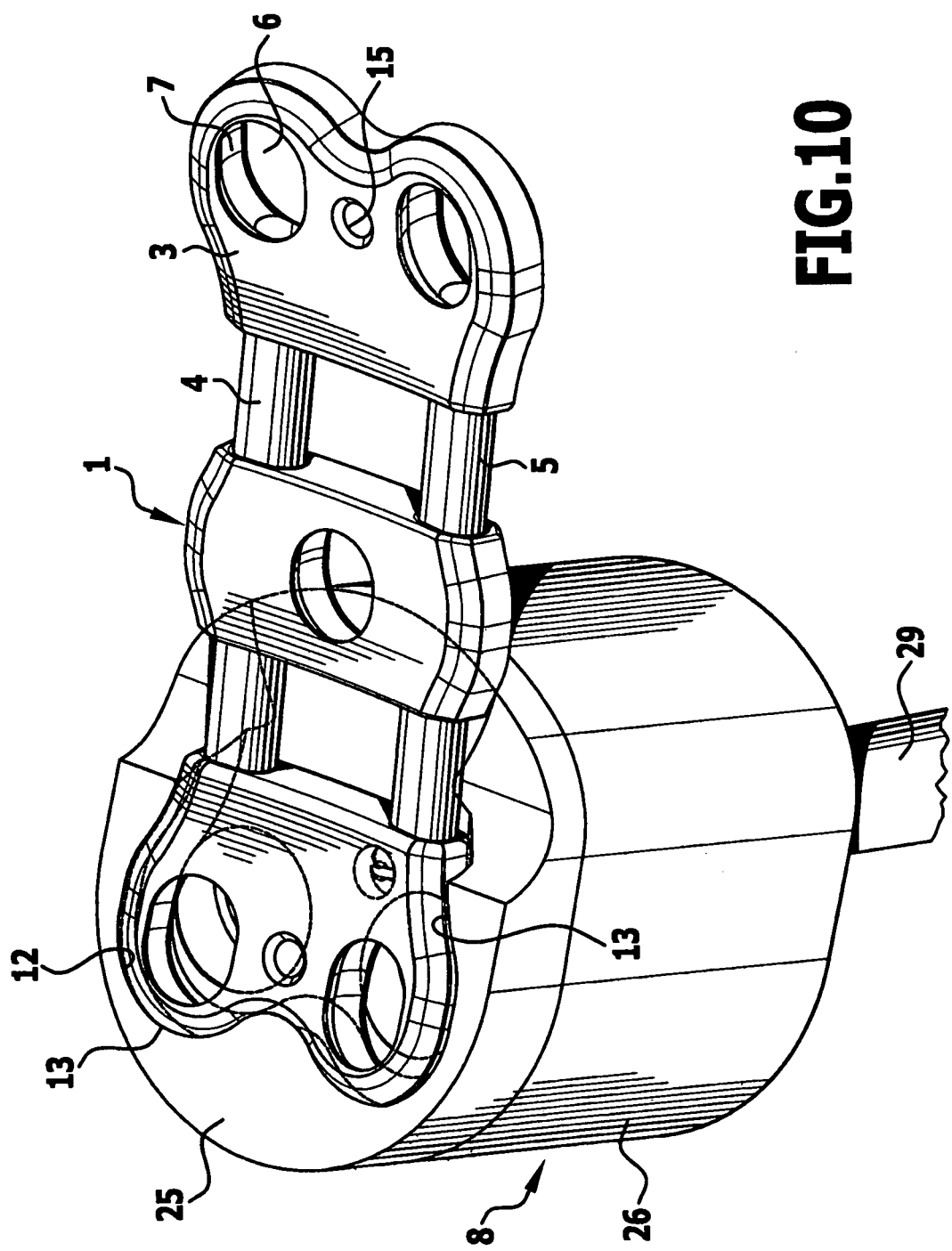
FIG. 10 shows a perspective view of the bone plate and the magazine of FIG. 9 from the underside.
Figure 11:
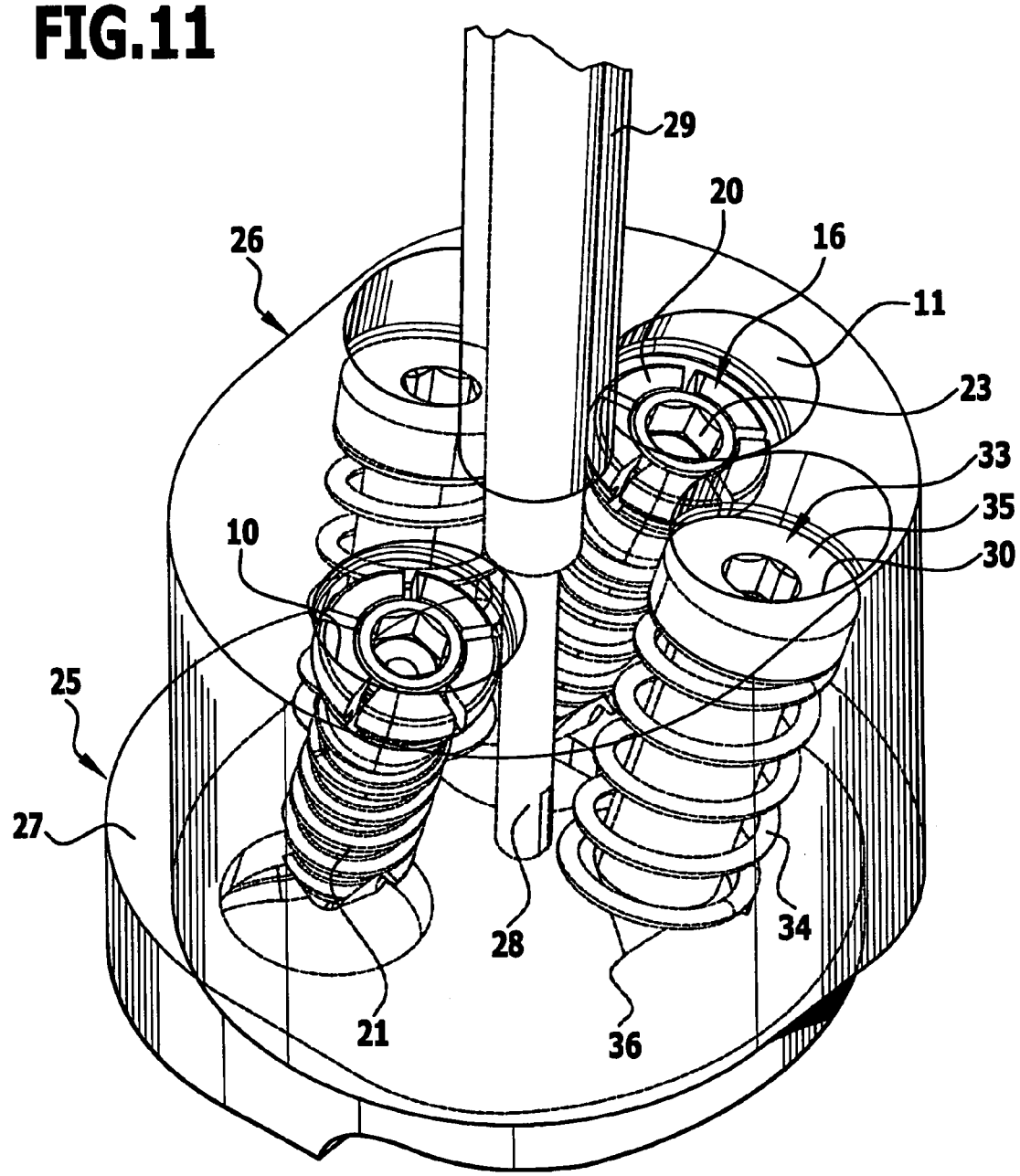
FIG. 11 shows a perspective view of the magazine of FIG. 9 with a housing rotated through 90° and bone screws in alignment with the screw-in openings.

A similar construction is also chosen for the embodiment of the magazine shown in FIGS. 9 to 11. Here, too, like parts are given like reference numerals.

Differently from the embodiments of FIGS. 1 to 6, the magazine 8 in the embodiment of FIGS. 7 to 11 comprises a holder 25 and a housing 26, which jointly replace the housing block 9 of the embodiment of FIGS. 1 to 6. The holder 25 serves to secure the magazine to the bone plate 1. On its underside, the holder is constructed in exactly the same way as described in conjunction with the embodiment of FIGS. 1 to 6, i.e., the holder 25 can be releasably snapped onto a respective end piece 2, 3 of the bone plate 1. The holder 25 has the shape of a plate with a flat, upper side 27 and the housing 26 is mounted on this plate-shaped holder, so that the housing 26 rests with its underside on the upper side 27. The housing 26 is rotationally connected to the holder 25. The axis of rotation extends perpendicularly to the upper side 27 and lies at the center of the upper side 27. To mount the housing 26 on the holder 25, a perpendicular bearing shaft 28 is provided, which protrudes upwards out of the housing 26 and serves as guide for a rotary tool 29, which can be pushed from above over the bearing shaft 28. The rotary tool engages the housing 26 in a rotationally fixed manner, which is not apparent from the drawings, so that upon rotation of the rotary tool 29, the housing 26 is rotated relative to the holder 25.

The arrangement may be chosen such that the housing 26 is axially secured to the holder 25. It may also be provided that the rotary tool 29 is axially fixedly connected to the housing 26, so that the rotary tool 29 may then also simultaneously serve as handling tool for the entire magazine and also for the bone plate with the magazine mounted thereon.

In the housing 26, in the embodiment shown in FIGS. 7 to 11, there are distributed over the circumference four receiving chambers 10, 11, 30, 31, which are selectively in alignment with the screw-in openings 6 in the bone plate 1 or offset in relation to these in accordance with the angular position of the housing 26. Herein, it is provided that the holder 25 comprises window-like through-openings 32 arranged above the screw-in openings 6, so that there is direct access to the corresponding screw-in openings 6 from the receiving chambers 10, 11 or 30, 31 in alignment with the screw-in openings.

As in the embodiment of FIGS. 1 to 6, bone screws 16 are held in their initial position in the receiving chambers 10, 11. In the case of alignment with the screw-in openings 6, the bone screws 16 can be advanced in the same way through these and then screwed into the bone lying underneath these.

In the embodiments of FIGS. 7 to 11, there are mounted for longitudinal displacement in the two other receiving chambers 30, 31 spike-shaped pins 33, which are surrounded by a helical spring 34. These pins are displaced by the helical spring 34, which is supported on a head-shaped widening 35 of the pins 33, into a proximal initial position and can be displaced against the force of the helical spring 34 in the distal direction in the receiving chamber 30, 31, so that in the case of alignment of this receiving chamber 30, 31 they project through the screw-opening 6 and with a tip 36 make a depression there in the bone lying underneath the bone plate 1. These therefore serve as a tool for punch-marking the bone.

In principle, it is also possible to arrange neither a spike-shaped pin nor a bone screw in one of the receiving chambers 30, 31, but to leave it empty and to then use the corresponding through-opening as guide for a drilling tool, a thread-cutting tool or the like. It is only essential that the corresponding receiving chamber 30, 31 be in alignment with a screw-in opening 6 when the housing 26 is in a corresponding angular position.

Figure 12:
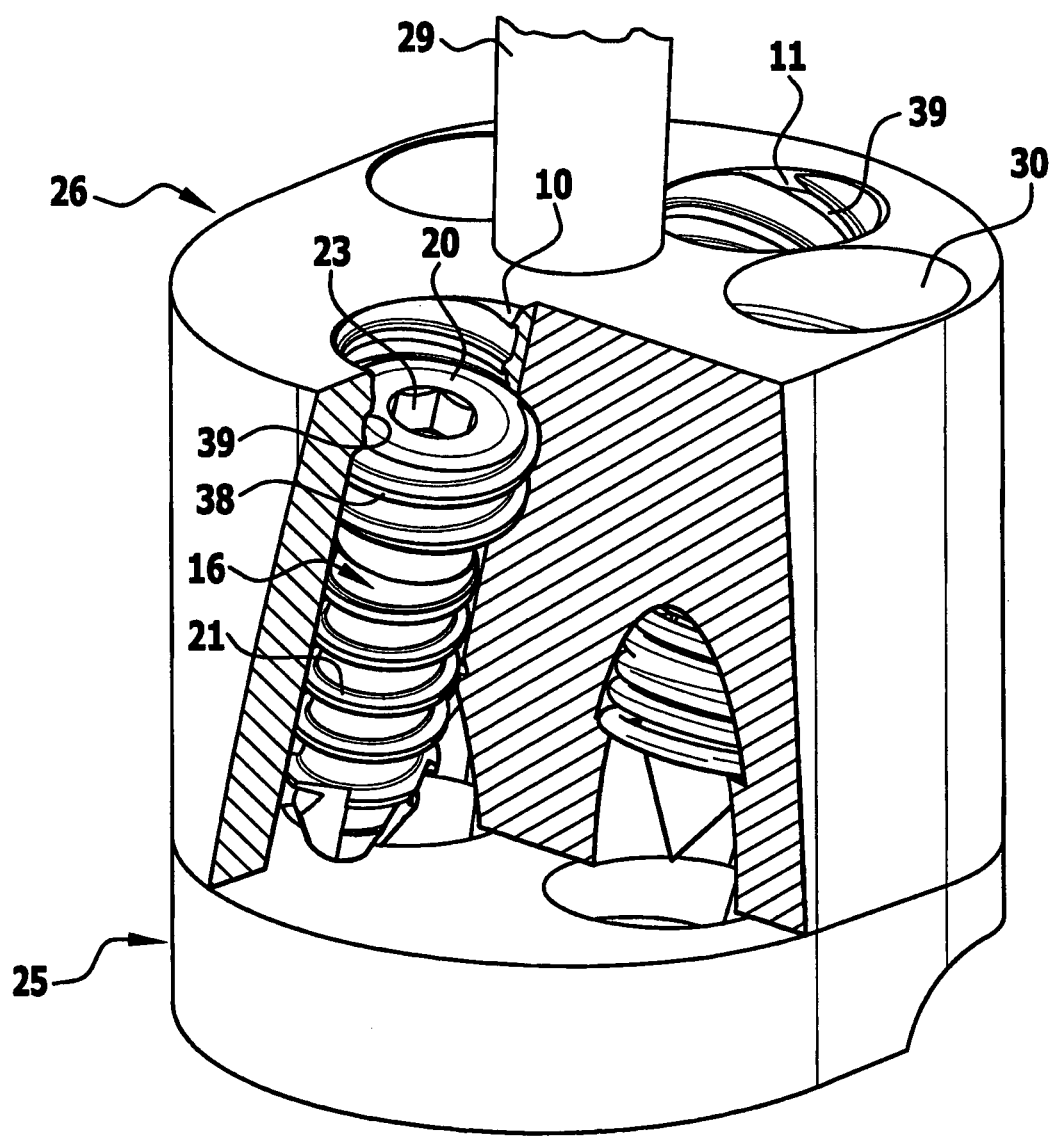
FIG. 12 shows a perspective view of a further preferred embodiment of a magazine similar to that of FIG. 9 in partially broken-open representation with a fixing device for the bone screw in the form of a thread.

In the embodiments described above, the bone screws are secured in the housing block by latching projections 18, which enter the circumferential groove 19 in the bone screw 16. In the embodiment of FIG. 12, in which a construction similar to that of the embodiments of FIGS. 9 to 11 is chosen, and in which like parts are given like reference numerals, the outer side of the head 20 of the bone screw 16 has an external thread 38, the pitch of which corresponds to the thread of the threaded shaft 21. There is machined in the inside wall of the receiving chambers 10, 11 on the upper side of the housing a corresponding internal thread 39 into which the external thread 38 of the head 20 is screwed, so that the bone screw is thereby fixed in the receiving chamber. This fixation is released by the screwing-in as the external thread 38 of the head 20 egresses from the internal thread 39 after a few rotations and can then be displaced without engagement in a widened area of the receiving chamber 10, 11 in the direction towards the bone. The turns of the internal thread 39 therefore protrude as projections into the cross section of the receiving chamber 10, 11. Such a configuration may, of course, also be used in the embodiments of FIGS. 1 to 6.

If, in a further preferred embodiment, the thread-shaped projection or recess is part of the thread of the threaded shaft, it may, for example, be provided that the core diameter in the threaded shaft is smaller than in the area of the projection or recess, so that overall in the head area the bone screw has a thickened core and is therefore still suited to press a bone plate against a bone when the bone screw is screwed into the bone. However, the outer diameter of the thread turns is identical in the area of the threaded shaft and in the area of the projections or recesses at the upper end of the bone screw, i.e., in this case, the bone screw has a continuous thread.

The magazine 8 of the embodiments described above may be supplied by itself as prefabricated, sterile unit, in which bone screws and, optionally, spike-shaped pins are already inserted and are located in the initial position therein. In principle, it is also possible to supply bone plates with magazines already appropriately mounted thereon as unit in sterile packaging so that the user need only place such a unit in the desired manner on the bone and is then immediately able to press the bone screws through the corresponding screw-in openings 6 and screw them in. There is no longer any need for insertion of the bone screws and guidance of the bone screws. These tasks are assumed by the magazine.

The invention claimed is:

1. Combination of a bone plate and a magazine for receiving at least one bone screw, comprising:
   a bone plate having at least one screw-in opening;
   a magazine for receiving at least one bone screw;
   a device for releasably securing said magazine to the bone plate;
   a receiving chamber extending continuously from an upper side to an underside of said magazine,
   a bone screw being arranged in said receiving chamber in such a way that when said magazine is secured to said bone plate, the distal tip of said bone screw is directed at a corresponding one of the at least one screw-in opening in said bone plate, a proximal end of said bone screw being accessible to a screwing-in tool from the upper side of said magazine; and
   a fixing device for releasably fixing said bone screw in said receiving chamber, the fixing device comprising at least one elastic latching projection and at least one latching recess cooperating with the at least one elastic latching projection.

2. Combination in accordance with claim 1, wherein the receiving chamber is in a form of a channel.

3. Combination in accordance with claim 1, wherein the receiving chamber forms a longitudinal guide for the bone screw, along which said bone screw is advanceable, while being screwed in, in a distal direction through the corresponding screw-in opening.

4. Combination in accordance with claim 1, wherein the bone screw abuts with a frictional fit on an inside wall of the receiving chamber and is thereby releasably held in the receiving chamber.

5. Combination in accordance with claim 1, wherein the at least one elastic latching projection extends into the receiving chamber and enters the at least one latching recess, the at least one latching recess being arranged on the bone screw.

6. Combination in accordance with claim 5, wherein the at least one elastic latching projection is arranged on a retaining element inserted into the receiving chamber.

7. Combination in accordance with claim 5, wherein the at least one elastic latching projection enters the at least one latching recess, the at least one latching recess being in a form of a circumferential groove provided on the bone screw.

8. Combination in accordance with claim 1, wherein the device releasably securing the magazine to the bone plate comprises elastic latching elements which hold the magazine by means of a snap-in connection on the bone plate.

9. Combination in accordance with claim 8, wherein the magazine carries on its underside the elastic latching elements which, when the magazine is mounted on the bone plate, engage around an outer side of said bone plate.

10. Combination in accordance with claim 9, wherein:
   the magazine has on its underside a receiving recess for receiving at least part of the bone plate,
   the elastic latching elements are formed by a rim of said receiving recess, the rim engages around the outer side of said bone plate when the bone plate is located in said receiving recess.

11. Combination in accordance with claim 1, wherein positioning projections and recesses are arranged on the magazine and on the bone plate, said positioning projections and recesses engaging with one another and thereby aligning the magazine relative to the bone plate.

12. Combination in accordance with claim 11, wherein the magazine carries on its underside a downwardly projecting positioning pin which enters a positioning opening on the bone plate when said magazine is mounted on said bone plate.

13. Combination in accordance with claim 1, wherein a handling grip is secured to the magazine.

14. Combination in accordance with claim 1, wherein the magazine comprises several adjacent receiving chambers, in each of which a bone screw is arranged in such a way that when the magazine is mounted on the bone plate, the bone screws are directed at corresponding ones of the at least one screw-in opening in the bone plate.

15. Combination in accordance with claim 1, wherein the magazine comprises a holder on which the device for releasably securing the magazine to the bone plate is arranged, and a housing which is displaceably mounted on the holder and comprises the receiving chamber or optionally several receiving chambers.

16. Combination in accordance with claim 15, wherein the housing comprises in addition to the receiving chamber or the receiving chambers for the bone screws at least one further through-opening which extends continuously from the upper side to the underside and, upon displacement of the housing, is alignable with one or more of the at least one screw-in opening in the bone plate.

17. Combination in accordance with claim 16, wherein the through-opening forms a receiving chamber for a spike-shaped pin which is mounted for longitudinal displacement in the receiving chamber.

18. Combination in accordance with claim 17, wherein the spike-shaped pin is displaced into a proximal end position by a spring and is displaceable in a distal direction against the action of the spring.

19. Combination in accordance with claim 16, wherein the housing is mounted for rotation on the holder in such a way that in different angular positions different receiving chambers and through-openings are alignable with the at least one screw-in opening.

20. Combination in accordance with claim 19, wherein a rotary handle is arranged on the housing.

\* \* \* \* \*